United States Patent [19]

Shields

[11] 4,199,500

[45] Apr. 22, 1980

[54] PEPTIDES RELATED TO SOMATOSTATIN

[75] Inventor: James E. Shields, Indianapolis, Ind.

[73] Assignee: Eli Lilly and Company, Indianapolis, Ind.

[21] Appl. No.: 962,502

[22] Filed: Nov. 20, 1978

[51] Int. Cl.² .................. C07C 103/52; A61K 37/00
[52] U.S. Cl. .......................... 260/112.5 S; 424/177
[58] Field of Search .................. 260/112.5 S; 424/177

[56] References Cited

U.S. PATENT DOCUMENTS

| | | | |
|---|---|---|---|
| 3,904,594 | 9/1975 | Guillemin et al. | 424/177 |
| 4,061,607 | 12/1977 | Shields | 260/112.5 S |
| 4,061,626 | 12/1977 | Shields | 260/112.5 S |
| 4,062,816 | 12/1977 | Shields | 260/112.5 S |
| 4,076,659 | 2/1978 | Shields | 260/112.5 S |
| 4,077,952 | 3/1978 | Sarantakis | 260/112.5 S |
| 4,087,390 | 5/1978 | Shields | 260/112.5 S |
| 4,100,117 | 7/1978 | Shields | 260/112.5 S |
| 4,123,425 | 10/1978 | Garsky | 260/112.5 S |

OTHER PUBLICATIONS

Rivier et al., Peptides 1976, 427–451.

*Primary Examiner*—Delbert R. Phillips
*Attorney, Agent, or Firm*—David E. Frankhouser; Arthur R. Whale

[57] ABSTRACT

The tetradecapaptides of the formula

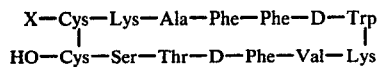

wherein X is H-Ala-D-Ala, H-D-Ala-Gly, or H-D-Val-Gly, or the non-toxic, pharmaceutically acceptable acid addition salts thereof; inhibit the secretion of growth hormone, while not materially inhibiting the secretion of insulin or glucagon. Intermediates used in the synthesis of the tetradecapeptides are also described.

8 Claims, No Drawings

PEPTIDES RELATED TO SOMATOSTATIN

This invention relates to synthetic peptides structurally related to somatostatin and to intermediates employed in the synthesis thereof.

Somatostatin is the cyclic disulfide tetradecapeptide of the formula:

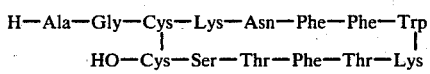
I

This peptide (I) has been identified as the "somatotropin-release inhibiting factor" (SRIF) which is secreted by the hypothalamus and regulates the secretion of pituitary growth hormone (GH) (somatotropin). [See Brazeau et al., *Science*, 179, 77 (1973), Burgus et al., *Proc. Nat. Acad. Sci. (USA)*, 70, 684 (1973), and Ling et al., *Biochemical and Biophysical Res. Communications*, 50, 127 (1973)]. The reduced form of somatostatin is the linear tetradecapeptide of the formula:

H-Ala-Gly-Cys-Lys-Asn-Phe-Phe-Trp-Lys-Thr-Phe-Thr-Ser-Cys-OH    II

The reduced form (II) has been prepared by total synthesis, [see Rivier et al., *C. R. Acad. Sci. p. Sci. Natur. (Paris)*, 276, 2737 (1973) and Sarantakis and McKinley, *Biochem. and Biophys. Res. Communications*, 54, 234 (1973)] and it (II) can be converted to somatostatin (I) by oxidation whereby a bridging bond is formed between the two sulfhydryls of the two cysteinyl amino acid residues in the tetradecapeptide.

Somatostatin inhibits the release of numerous hormones in addition to growth hormone, including those from the pituitary (prolactin), the gut (gastrin, cholecystokinin, and secretin), and the pancreas (insulin and glucagon).

Various polypeptides which may be regarded as structural modifications of somatostatin have been prepared synthetically and are reported in the chemical literature. Such polypeptides have certain structural features in common with somatostatin and differ from somatostatin in that specific amino acid residues or functional groups originally present in the somatostatin molecule are either missing or are replaced by other amino acid residues or functional groups. The present invention relates to novel synthetic biologically active polypeptides which may be regarded as structural modificiations of somatostatin. The polypeptides of the invention differ from somatostatin in the following respects:

(a) The Ala$^1$-Gly$^2$ segment is replaced by Ala-D-Ala, D-Ala-Gly, or D-Val-Gly;
(b) The Asn$^5$ residue is replaced by Ala;
(c) The Trp$^8$ residue is replaced by D-Trp;
(d) The Thr$^{10}$ residue is replaced by Val, and
(e) The Phe$^{11}$ residue is replaced by D-Phe.

All optically active amino acids and amino acid residues in the polypeptides depicted and described herein are in the natural or L-configuration, unless otherwise noted. The symbols identifying the amino acids and the amino acid residues in the polypeptides described herein are those adopted by the IUPAC-IVB Committee on Biochemical Nomenclature Recommendation (1971), and are described in the *Archives of Biochemistry and Biophysics*, 150, 1–8 (1972).

In its first aspect, the invention for which a patent is solicited comprises tetradecapeptides of the formula:

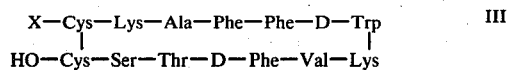
III wherein: X is H-Ala-D-Ala-, H-D-Ala-Gly, or H-D-Val-Gly; or a non-toxic, pharmaceutically acceptable acid addition salt thereof.

The peptides of Formula III are biologically active and inhibit the secretion of growth hormone without materially inhibiting the secretion of insulin and glucagon, as demonstrated in vivo in laboratory animals using standard pharmacological test procedures. Because of this specificity, the peptides are especially useful in the treatment of diabetes and of other pathological conditions (e.g. acromegaly) characterized by the abnormally high secretion of growth hormone.

A preferred embodiment of the peptides defined by Formula III is that wherein X is H-Ala-D-Ala.

In its second aspect, the invention contemplates the linear form (IV) of the tetradecapeptides of Formula III:

X-Cys-Lys-Ala-Phe-Phe-D-Trp-Lys-Val-D-Phe-Thr-Ser-Cys-OH    IV or a non-toxic acid addition salt thereof; wherein X has the meanings hereinbefore defined with respect to Formula III. The linear peptides defined by Formula IV are precursors in the preparation of the peptides of Formula III. In the cyclic form (III), the two cysteine residues (Cys$^3$ and Cys$^{14}$) are linked by means of a disulfide bond formed between the side chain sulfhydryl functions. In the linear form, the two cysteine residues are not linked and the side-chain sulfhydryl functions are free. The cysteine residues each contain a free sulfhydryl group.

In a third aspect, the invention contemplates the protected peptides of Formula V:

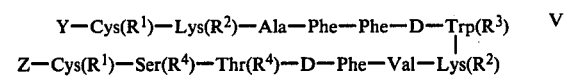
V wherein:
Y is R-Ala-D-Ala, R-D-Ala-Gly, or R-D-Val-Gly wherein R is H or an α-amino protecting group;
R$^1$ is a sulfhydryl protecting group;
R$^2$ is an ε-amino protecting group;
R$^3$ is hydrogen or formyl;
R$^4$ is a hydroxyl protecting group; and
Z is —OH, —OCH$_3$, or —O—CH$_2$-[polystyrene resin]; and, when R is H, the non-toxic acid addition salts thereof.

The peptides of Formula V are intermediates in the synthesis or the peptides of Formula III and IV.

In the synthesis of the peptides of Formula III, the peptide chain is built stepwise by the sequential coupling of individual amino acids commencing from the C-terminal end of the chain. During each coupling, the amino acids must be protected at the α-amino group and, if necessary, at reactive side-chain functional groups to prevent the formation of undesirable side products. In the peptides of Formula V, the protecting groups represented by R, R$^1$, R$^2$, and R$^4$ were employed to block reactive α-amino or side-chain groups in the individual amino acids during their incorporation into the peptide chain. The protecting groups represented by R, $R^1$, $R^2$, and $R^4$ can, therefore, be any group known in the art to be useful for the stepwise synthesis of polypeptides. Such groups are well-known, and the selection of a particular protecting group and its method of use will be readily apparent to a peptide chemist of ordinary skill. Illustrative examples of protecting groups for R, $R^1$, $R^2$ and $R^4$ are set forth below:

A. For an α-amino group present in the N-terminal amino acid residue, R may be: (a) acyl-type groups, such as formyl, trifluoracetyl, phthalyl, p-toluene sulfonyl (tosyl), benzenesulfonyl, nitrophenylsulfenyl, etc; (b) aromatic urethane-type groups, such as benzyloxycarbonyl and substituted benzyloxycarbonyl, for example: p-chlorobenzyloxycarbonyl, p-bromobenzyloxycarbonyl, p-nitrobenzyloxylcarbonyl, and p-methoxybenzyloxycarbonyl, o-chlorobenzyloxycarbonyl, 2,4-dichlorobenzyloxycarbonyl, 2,6-dichlorobenzyloxycarbonyl, etc; (c) aliphatic urethane-type groups such as t-butyloxycarbonyl, t-amyloxycarbonyl, isopropyloxycarbonyl, 2-(p-biphenyl) isopropyloxycarbonyl, allyloxycarbonyl, etc; (d) cycloalkyl urethane-type groups such as cyclopentyloxycarbonyl, cyclohexyloxycarbonyl, cycloheptyloxycarbonyl, adamantyloxycarbonyl, etc; (e) thio urethane-type groups such as phenylthiocarbonyl; (f) alkyl-type groups such as triphenylmethyl, or (g) trialkylsilane groups, such as trimethylsilane. The preferred α-amino protecting groups defined by R is t-butyloxycarbonyl (BOC).

B. For the sulfhydryl group present in cysteine, $R^1$ may be benzyl and substituted benzyl (e.g. 3,4-dimethylbenzyl, p-methoxybenzyl, p-methylbenzyl, p-chlorobenzyl, p-nitrobenzyl), trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, etc. The preferred sulfhydryl protecting group defined by $R^1$ is p-methoxybenzyl (MBzl).

C. For the ε-amino protecting group present in lysine, $R^2$ may be one of the groups mentioned hereinabove for the protection of an α-amino group. Typical groups include for example, benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, etc. The preferred ε-amino protecting group defined by $R^2$ is o-chlorobenzyloxycarbonyl (ClBzl).

D. For the hydroxyl group of serine or threonine, $R^4$ may $C_1$-$C_4$ alkyl (e.g. methyl, ethyl, t-butyl), benzyl, substituted benzyl (e.g. p-mmethoxybenzyl, p-nitrobenzyl, p-chlorobenzyl, o-chlorobenzyl), $C_1$-$C_3$ alkanoyl (e.g. formyl, acetyl, propionyl), triphenylmethyl, or benzoyl. The preferred hydroxy protecting group defined by $R^4$ is benzyl (Bzl).

The group $R^3$ represents either hydrogen of formyl substituted on the nitrogen of the indole ring of tryptophan. The use of formyl as a protecting group is optional. $R^3$ is preferably hydrogen.

In Formula V, when Z represents "—O—$CH_2$-[polystyrene resin]" the peptide chain is attached to the polystyrene resin by means of an ester linkage, (—Cys—O—$CH_2$—) formed between the carboxyl group of the C-terminal cysteine moiety and one of the methylene groups present on the resin matrix as sites for such attachment. The polystyrene resin is a styrene polymer which is cross linked by the addition of about 0.5 to about 3% divinylbenzene and which is chloromethylated or hydroxymethylated to provide sites for ester formation. An example of a hydroxymethylated resin is described by Bodanszky et al. *Chem. Ind.* (London) 38, 1597–98 (1966). A chloromethylated polystyrene resin is commercially available from Lab System, Inc., San Mateo, California. The resin is also described by Stewart et al *Solid Phase Peptide Synthesis*, Freeman and Co., San Francisco, California, pp. 1–6.

The tetradecapeptides of this invention can be made either by classical (solution) methods or by the solid phase method using techniques generally known in the art for forming peptide bonds. The peptide can be assembled either by coupling each amino acid separately or by coupling appropriate pre-formed peptide segments in the desired order.

The preferred method of preparation of the peptides of Formula III, and of the intermediates of Formula IV and V is by the solid phase technique in which the amino acid sequence is built sequentially from an initial, insoluble resin-supported C-terminal amino acid. Techniques for the solid phase method are described by J. Stewart etal. *Solid Phase Peptide Synthesis*, Freeman and Co., San Francisco, 1969.

In general, in the solid phase method, the amino acid corresponding to the C-terminal amino acid residue of the desired peptide is anchored to an insoluble resin support, and the peptide chain is then formmed beginning at the resin-supported C-terminal amino acid by introducing the individual amino acids one at a time until the desired amino acid sequence is achieved. Alternatively, small peptide fragments can be prepared and introduced into the peptide chain in the desired order. The peptide chain remains attached to the resin throughout the synthesis, and, upon completion of the chain, the peptide is cleaved from the resin.

The amino acids are coupled using techniques well-known in the art for the formation of a peptide bond. One method is to convert the amino acid to a derivative that will render the carboxyl group more reactive to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutylchloroformate, pivaloyl chloride, or like acid chloride. Alternatively, the amino acid can be converted to an active ester such as a 2,4,5-trichlorophenyl ester, a pentachlorophenyl ester, a p-nitrophenyl ester, an ester formed from N-hydroxysuccinimide, or an ester formed from 1-hydroxybenzotriazole.

Another method is to perform the coupling reaction with a suitable coupling agent, such as N,N'-dicyclohexylcarbodiimide (DCC) or N,N'-diisopropylcarbodiimide (DIC). Other appropriate coupling agents will be apparent to those skilled in the art. [See Schroder and Lubke, *The Peptides*, Academic Press, 1965, Chapter III.]

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g. sulfhydryl, ε-amino, and hydroxyl), and such functional groups must also be protected both during the initial coupling of the amino acid containing the side-chain group and during the coupling of subsequent amino acids. Suitable protecting groups are known in the art [See for example, *Protective Groups In Organic Chemistry*, M. McOmie, Editor, Plenum Press, N.Y., 1973.]

In selecting a particular protecting group the following conditions must be observed: An α-amino protecting group must: (1) be stable and render the α-amino function inert under the conditions employed in the coupling reaction, and (2) must be readily removable after the coupling reaction under conditions that will not remove the side chain protecting groups or alter the structure of the peptide fragment. A side chain protecting group must: (1) be stable and render the side chain functional group inert under the conditions employed in the coupling reaction, (2) be stable under the conditions employed in removing the α-amino protecting group, and (3) be readily removable upon completion of the desired amino acid sequence under reaction conditions that will not alter the structure of the peptide chain.

It will be apparent to those skilled in the art that the protecting groups known in the art to be useful for peptide synthesis will vary in their reactivity towards the acidic agents employed for their removal. For example, certain protecting groups, such as triphenylmethyl and 2-(p-biphenyl)isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl are less labile and require moderately strong acids (such as trifluoroacetic, hydrochloric, or boron-trifluoride in acetic acid) for their removal. Still other protecting groups, such as benzyloxycarbonyl, halobenzyloxycarbonyl, p-nitrobenzyloxycarbonyl, cycloalkoxycarbonyl, and isopropyloxycarbonyl, are even less labile and require strong acids, such as hydrogen fluoride, hydrogen bromide, boron trifluoroacetate in trifluoroacetic acid for their removal.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal cysteine moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid hydrogen fluoride. The reagent will not only cleave the peptide from the resin but will also remove all protecting groups. Hence, use of this reagent will directly afford the fully deprotected linear form of the peptide. When it is desired to cleave the peptide without removing protecting groups, the protected peptide-resin can undergo methanolysis to give the protected linear peptide in which the C-terminal carboxyl group is methylated. The methyl ester can then be hydrolyzed under mild, alkaline conditions to give the free C-terminal carboxyl. The protecting groups on the peptide chain can then be removed by treatment with a strong acid, such as liquid hydrogen fluoride. A particularly useful technique for methanolysis is that of G. Moore et al., *Peptides*, Proc. 5th Amer. Pept. Symp., M. Goodman and J. Meinhofer, Eds., John Wiley, N.Y., 1977, pp. 518–521 in which the protected peptide-resin is treated with methanol and potassium cyanide in the presence of crown ether.

Another method for cleaving the protected peptide from the resin is by ammonolysis or by treatment with hydrazine. The resulting C-terminal amide or hydrazide can be hydrolyzed to the free C-terminal carboxyl, and the protecting groups can be removed conventionally.

It will also be recognized that the protecting group present on the N-terminal α-amino group may be removed preferentially either before or after the protected peptide is cleaved from the resin support.

Upon cleavage from the resin and the removal of all protecting groups, the product obtained is in the form of the linear tetradecapeptide. The linear tetradecapeptide can be cyclized to the final cyclic tetradecapeptide (III) by means of an oxidizing agent capable of converting the two sulfhydryl groups of $Cys^3$ and $Cys^{14}$ to the disulfide bond. Both exposure to air or treatment with potassium ferricyanide may be used to effect such oxidation. When air is employed, the pH of the medium should be about 2.5 to about 9.0 and preferably about 7.0 to 7.6 and the concentration of the peptide should not be above 0.4 mg/ml. A concentration of about 50 μg/ml is preferred.

For pharmacological purposes, the peptides of this invention can be administered in the form of an acid addition salt prepared by reaction with an appropriate organic or inorganic acid which is non-toxic and acceptable for pharmaceutical purposes. Suitable acids are well known in the art. Illustrative of such acids are hydrochloric, hydrobromic, sulfuric, sulfonic, tartaric, fumaric, glycolic, succinic, malonic, citric, maleic, acetic, phosphoric, benzoic, ascorbic, nitric, p-toluenesulfonic, benzenesulfonic, naphthalenesulfonic, propionic, and the like. Acetic acid is preferred.

The preferred method for the solid phase synthesis of the peptides of Formula III and the intermediates thereto, is illustrated by the Examples. In this method, α-amino and sulfhydryl protected cysteine (Boc-Cys(MBzl)-OH) is first attached to chloromethylated polystyrene resin according to the method of B. Gisin *Helv. Chim. Acta.*, 56, 1476 (1173) wherein the cesium salt of the protected cysteine is reacted with the chloromethylated polystyrene resin in dimethylformamide. The t-butyloxycarbonyl protecting group is then removed by treatment with trifluoroacetic acid in chloroform-methylene chloride. Individual protected amino acids are then coupled sequentially beginning at the resin-supported C-terminal cysteine until the desired tetradecapeptide is achieved. Throughout the synthesis, N,N'-dicyclohexylcarbodiimide is used as the coupling agent, and t-butyloxycarbonyl (Boc) is used as the α-amino protecting group. The side chain protecting groups are: p-methoxybenzyl (MBzl) for the sulfhydryl group of cysteine; o-chlorobenzyloxycarbonyl (Clz) for the ε-amino of lysine; and benzyl (Bzl) for the hydroxyl of serine and threonine. Trifluoroacetic acid in methylenechloride is employed to remove preferentially the t-butyloxycarbonyl protecting group. After each deprotection, the side-chain protected peptide is neutralized with triethylamine.

Upon completion of the desired amino acid sequence, the resulting tetradecapeptide is deprotected and removed from the polystyrene resin by treatment with liquid hydrogen fluoride in the presence of anisole and ethylmercaptan. The resulting linear tetradecapeptide (IV) is readily converted to the cyclic tetradecapeptide (V) by exposure of a solution of the linear tetradecapeptide (IV) to atmospheric oxygen. The cyclic tetradecapeptide is purified by chomotography using a Sephadex G-25 Fine Column.

For pharmacological use, the tetradecapeptides of Formula III may be administered alone on in combination with pharmaceutically acceptable carriers or excipients. Suitable pharmaceutical carriers will be apparent to those skilled in the art. Administration may be orally or parenterally by methods conventional in the art of medicine. The method of making and using the peptides of the invention are illustrated in the following Examples.

EXAMPLE 1

N-t-Butyloxycarbonyl-L-(S-p-methoxybenzyl)cysteine hydroxymethyl-polystyrene resin ester Chloromethylated polystryene resin is esterified by the method of F. Gisin *Helv. Chim. Acta.* 56, 1976 (1973).

A solution of the cesium salt of t-butyloxycarbonyl-L-(S-p-methoxybenzyl)cysteine (64.4 m moles) in dimethylformamide (DMF) (1000 ml.) is stirred with chloromethylated polystyrene resin (Lab Systems, Inc.) (100 g.; 0.75 m. mole Cl/g.) at room temperature for six days. The resin is separated by filtration and washed with 85% DMF-15% water and then with DMF alone. This wash sequence is repeated two additional times. The resin is next washed three times with 95% ethanol. After three more washings with DMF, the resin is suspended in DMF (1000 ml.), and the suspension is stirred with cesium acetate (16 g.; 83.4 m. mole) at room temperature for six days. The resin is separated by filtration and washed with 85% DMF-15% water and with DMF alone. This sequence is repeated two additional times. The resin is suspended in chloroform contained in a separatory funnel. Fines are removed by drawing off liquid. This separation is repeated five additional times. The resin is collected by filtration and washed thoroughly with 95% ethanol, afterwhich it is dried overnight in vacuo at 40° C. to give 115.03 g. of the title product. A portion of the resin is assayed for cysteine after hydrolysis using a 1:1 mixture of conc. hydrochloric acid-dioxane in the presence of a small amount of dimethylsulfoxide.

Found: 0.304 m. mole cysteine per g. of resin.

EXAMPLE 2

N-t-Butyloxycarbonyl-L-alanyl-D-alanyl-L-(S-p-methoxybenzyl)cysteinyl-L-(N$^\epsilon$-o-chlorobenzyloxycarbonyl)lysyl-L-alanyl-L-phenylalanyl-L-phenylalanyl-D-tryptophyl-L-(N$^\epsilon$-o-chlorobenzyloxycarbonyl)lysyl-L-valyl-D-phenylalanyl-L-(O-benzyl)threonyl-L-(O-benzyl)seryl-L-(S-p-methoxybenzyl)cysteine hydroxymethylpolystyrene resin ester N-t-Butyloxycarbonyl-L-(S-p-methoxybenzyl) cysteine hydroxymethyl-polystyrene resin ester (10.0 g.), as prepared in Example 1, is placed in the reaction chamber of a Beckman 990 peptide synthesizer and is treated according to Schedule A (set forth below), N-t-butyloxycarbonyl-L-(O-benzyl) serine being employed as the amino acid added in Step 11 thereof. After the final methylene chloride wash (Step 18), the product is washed three times with dimethylformamide (DMF) and is re-coupled by following Step 11 of Schedule A.

The product is then washed three times with DMF and is retreated by following Steps 12–18 of Schedule A.

In a similar manner, the following protected amino acids are incorporated sequentially into the peptide resin:

N-t-butyloxycarbonyl-L-(O-benzyl)threonine
N-t-butyloxycarbonyl-D-phenylalanine
N-t-butyloxycarbonyl-L-valine
N-t-butyloxycarbonyl-L-(N$^\epsilon$-o-chlorobenzyloxycarbonyl)lysine
N-t-butyloxycarbonyl-D-tryptophane
N-t-butyloxycarbonyl-L-phenylalanine
N-t-butyloxycarbonyl-L-phenylalanine
N-t-butyloxycarbonyl-L-alanine*
N-t-butyloxycarbonyl-L-(N$^\epsilon$-o-chlorobenzyloxycarbonyl)lysine
N-t-butyloxycarbonyl-L-(S-p-methoxybenzyl)cysteine
N-t-butyloxycarbonyl-D-alanine*
N-t-butyloxycarbonyl-L-alanine*

*Steps 10–18 of Schedule A are not repeated during the incorporation of BOC-Ala or BOC-D-Ala.

After incorporation of the N-terminal amino acid residue (L-alanine), the peptide resin is dried in vacuo. An amino acid analysis (obtained by refluxing a portion of the peptide for 72 hours in conc. hydrochloric acid-dioxane, 1:1) gives the following results, lysine being employed as the standard: Thr 1.06; Ser, 0.98; 3 Ala, 3.06; Val, 0.92; 3 Phe, 3.24; 2 Lys, 2.00.

SCHEDULE A [Protocol for the removal of the t-butyloxycarbonyl α-amino protecting group and the coupling of the amino acid to the peptide-resin]
1. Wash with CHCl$_3$, three times.
2. To remove the t-butyloxycarbonyl α-amino protecting group, treat with a mixture of trifluoroacetic acid (28.8%), CH$_2$Cl$_2$ (17.5%), and triethylsilane (5.8%) for twenty minutes. Repeat one time.
3. Wash with CHCl$_3$ two times.
4. Wash with CH$_2$Cl$_2$, one time.
5. Wash with 90% t-BuOH 10% t-AmOH, three times.
6. Wash with CH$_2$Cl$_2$, three times.
7. For neutralization, treat with 3% triethylamine in CH$_2$Cl$_2$, three times.
8. Wash with CH$_2$Cl$_2$, three times.
9. Wash with 90% t-BuOH -10% t-AmOH, three times.
10. Wash with CH$_2$Cl$_2$, three times.
11. To couple the amino acid, treat with the protected amino acid (1.0 m. mole/g. resin) and N,N'-dicyclohexylcarbodiimide (1.0 m. mole/g. resin) in CH$_2$Cl$_2$. Allow two-hour reaction time.
12. Wash with CH$_2$Cl$_2$, three times.
13. Wash with 90% t-BuOH-10% t-AmOH.
14. Wash with CH$_2$Cl$_2$, three times.
15. For neutralization, treat with 3% triethylamine in CH$_2$Cl$_2$, three times.
16. Wash with CH$_2$Cl$_2$, three times.
17. Wash with 90% t-BuOH-10% t-AmOH, three times.
18. Wash with CH$_2$Cl$_2$, three times.

In Schedule A, the following symbols are used:
CHCl$_3$ = chloroform
CH$_2$Cl$_2$ = methylene chloride
t-BuOH = t-butylalcohol
t-AmOH = t-amyl alcohol The volume of solvent employed for each step is eight ml./g. of resin. Unless otherwise noted, the contact time for each step is three minutes.

EXAMPLE 3

L-Alanyl-D-alanyl-L-cysteinyl-L-lysyl-L-alanyl-L-phenylalanyl-L-phenylalanyl-D-tryptophyl-L-lysyl-L-valyl-D-phenylalanyl-L-threonyl-L-seryl-L-crysteine The protected peptido-resin prepared in Example 2 (3.086 g., at a substitution level of 0.175 m. mole/g. resin) is mixed with anisole (6.4 ml.) and ethyl mercaptan (6.4 ml). The mixture is cooled with liquid nitrogen and liquid hydrogen fluoride (72 ml.) is added by distillation. The mixture is then brought to 0° C. and is stirred for two hours. Removal of hydrogen fluoride by distillation gives a residue to which is added ether at 0° C. The solid is collected, washed with ether, and dried. The peptide is separated from the resin by extracting the solid with 1 M acetic acid and 50% acetic acid. The extract is lyophilized in the dark to dryness. A mixture of 0.2 M acetic acid (10 ml) and glacial acetic acid (8 ml) is added to the dry material, and the suspension is warmed to effect solution. The material is not completely soluble. Insolubles are removed by filtration. The filtrate is chromatographed through a Sephadex G-25 Fine column under the following conditions—solvent; degassed 0.2 M acetic acid; column size: 7.5×150 cm; temperature: 26° C.; flow rate: 685 ml/hour; fraction volume: 21.7 ml.

A plot of absorbance at 280 mµ of each fraction versus fraction number shows a broad peak with a following shoulder. UV spectrographic analysis indicates that the fractions represented by the broad peak contain the desired product. Hence, fractions 249–273 (5382–5924 ml, peak 5715 ml) are combined. UV spectrographic analysis of a sample of the combined fractions indicates that 159 mg. of the product is obtained. Recovery: 18.3% Free sulfhydryl content: 82.2% of theoretical (by Ellman titration).

EXAMPLE 4

L-Alanyl-D-alanyl-L-cysteinyl-L-lysyl-L-alanyl-L-phenylalanyl-L-phenylalanyl-D-tryptophyl-L-lysyl-L-valyl-D-phenyl-alanyl-L-threonyl-L-seryl-L-cysteine cyclic (3->14) disulfide The linear peptide prepared in Example 3 is air oxidized to the corresponding cyclic peptide by the following procedure:

The combined fractions obtained in Example 3 (542 ml, theoretically containing 159 mg. of peptide) are diluted with 2614 ml of distilled water to achieve a final solution having a concentration of 50 µg/ml. Sufficient concentrated ammonium hydroxide is added to bring the pH to 6.7. The solution is then stirred at room temperature in the dark for 64 hours at which time Ellman titration of an aliquot indicates complete oxidation.

The solution is concentrated in vacuo to a volume of about 30 ml. Glacial acetic acid (30 ml) is added and the solution is desalted by chomatography on a Sephadex G-25 Fine Column under the following conditions—solvent: degassed 50% acetic acid; column size: 5.0×210 cm; temperature: 26° C.; flow rate: 136 ml/hour; fraction volume: 16.1 ml.

A plot of absorbance at 280 mµ of each fraction versus fraction number shows two large peaks. The first represents the aggregated forms of the peptide, while the second represents monomeric material. Fractions 127–138 (2029–2222 ml.) are combined and lyophilized to dryness in the dark. The resulting solid is dissolved in degassed 0.2 M acetic acid (15 ml.) and the solution is chromatographed on a Sephadex G-25 Fine column under the following conditions—solvent; degassed 0.2 M acetic acid; column size: 5.0×150 cm; temperature; 26° C.; flow rate: 470 ml/hour; fraction volume: 16.45 ml.

A plot of absorbance at 280 mµ of each fraction versus fraction number shows a single peak with a back side shoulder. UV spectrographic analysis indicates that the fractions represented by the main part of this peak comprise the desired product. Fractions 164–174 (2681–2862 ml; peak, 2766 ml) are combined and lyophilized in the dark to give the title peptide. UV spectrographic analysis of the combined fractions before lyophilization indicated that 31.4 mg. of the product is obtained. Recovery, 19.7% (from the linear form).

Amino acid analysis: 3 Ala, 2.82; 2 Cys, 1.44; 2 Lys, 2.0; 3 Phe, 2.97; D-Trp, 0.96; Val, 0,95; Thr, 0.97; Ser. 0.84.

The above results are expressed as ratios to Lys/2. All values are the average of 2 hydrolyses, with no added scavengers. The value for D-Trp was determined by UV spectrographic analysis based on the concentration of the solution submitted for analysis.

EXAMPLE 5

The effects of the tetradecapeptides of Formula III on the inhibition of growth hormone, insulin, and glucagon can be elicited and demonstrated in the following test procedures:

A. Growth Hormone Inhibition In Rats:

This test is a modification of the method of P. Brazeau et al. *Endocrinology*, 94, 184 (1974). Male rats (weighing 100–110 g.) are divided into three groups of eight rats each. Each rat is administered sodium pentobarbital at a dose of 4 mg/rat (I.P.) to stimulate growth hormone (GH) secretion. Simultaneously, one group of rats receives the test compound (S.C.); the second group receives somatostatin (S.C.); and the third group (control) receives saline (S.C.). Twenty-minutes later, the animals are decapitated and blood samples are collected. The serum concentration of growth hormone (GH) is determined by radioimmunoassay. The mean GH concentration (± standard error of the mean) is calculated for each group. The percent inhibition of GH release (as compared to saline controls) is then calculated for the test compound and for somatostatin. When tested as above-described, the peptide of Example 4 (D-Ala$^2$, Ala$^5$, D-Trp$^8$, Val$^{10}$, D-Phe$^{11}$-Somatostatin) representative of the peptides of Formula III, gave the results set forth below in Table I:

Table I

| Peptide | Growth Hormone Inhibition | | % Inhibition* |
|---|---|---|---|
| | Dose (mg/kg) | Serum Growth Hormone Conc. Mean ± SEM mg/ml | |
| Example 4, | 50 | 97 ± 39 | 66 |
| | 2 | 61 ± 24 | 7.8 |
| Somatostatin | 50 | 19 ± 11 | 93 |
| | 2 | 105 ± 69 | 63 |
| Saline (control) | — | 281 ± 110 | — |

*As compared to control.

B. Insulin and Glucagon Inhibition In Dogs:

A normal dog is fasted overnight. An intravenous (I.V.) infusion of the test compound (dissolved in saline) is begun. Thirty minutes thereafter an additional infusion of L-alanine (dissolved in saline) is begun and is continued for a total of 15 minutes so that a total dose of about 1 mmole of L-alanine per kg. body weight is given. Infusion of the test compound is continued for an additional 15 minute period.

Blood samples are taken periodically before (at −20, −10 and −1 minutes) and after (5, 10, 15, 30, 35, 40, 45, 50, 60, 90, 120 and 150 minutes) the start of the infusion of the test compound. The serum insulin and serum glucagon concentrations in the blood are determined by radioimmunoassay. A plot is made of the glucagon and insulin concentrations versus time. The plot obtained from the test compound is compared to plots obtained from somatostatin and saline (controls) in similar experiments.

Infusion of L-alanine (in the absence of somatostatin or active test compound) causes an abrupt increase in serum insulin and glucagon concentrations. The concentrations return to basal levels after the L-alanine infusion is terminated. Infusion of somalostatin (alone) causes a decrease in basal serum concentrations of insulin and glucagon. In the presence of L-alanine, somatostatin inhibits the increase in insulin and glucagon concentrations induced by the L-alanine.

When tested according to the procedure above-described the peptide of Example 4 illustrative of the peptides of Formula III, produced no significant inhibition of insulin or glucagon concentration at a dose of 0.237 μg/Kg./min.

What is claimed is:

1. A cyclic tetradecapeptide of the formula:

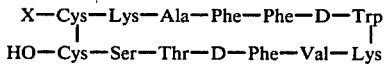

wherein X is H-Ala-D-Ala, H-D-Ala-Gly, or H-D-Val-Gly; or a non-toxic pharmaceutically acceptable acid addition salt thereof.

2. The compound as defined in claim 1 which is:

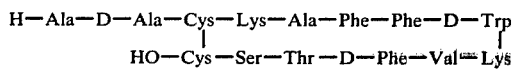

3. A linear tetradecapeptide of the formula:

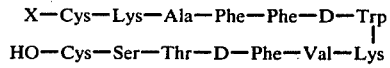

wherein X is H-Ala-D-Ala, H-D-Ala-Gly, or H-D-Val-Gly; or a non-toxic, pharmaceutically acceptable acid addition salt thereof.

4. The compound as defined in claim 3 which is

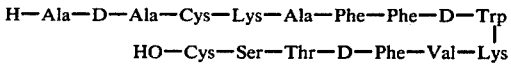

5. A linear tetradecapeptide of the formula:

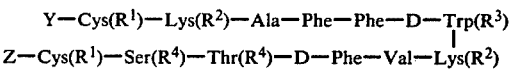

wherein:
Y is R-Ala-D-Ala, R-D-Ala-Gly, or R-D-Val-Gly wherein R is H or an α-amino protecting group;
$R^1$ is a sulfhydryl protecting group;
$R^2$ is a ε-amino protecting group;
$R^3$ is hydrogen or formyl;
$R^4$ is a hydroxyl protecting group; and
Z is —OH, —OCH$_3$, or —O—CH$_2$-[polystyrene resin], and, when R is H, the non-toxic acid addition salts thereof.

6. A compound as defined in claim 4 wherein Z is —O—CH$_2$-[polystyrene resin].

7. A compound as defined in claim 5 wherein R(of Y) is t-butyloxycarbonyl, $R^1$ is p-methoxybenzyl, $R^2$ is o-chlorobenzyloxycarbonyl, $R^3$ is H, and $R^4$ is benzyl.

8. The compound as defined in claim 7 wherein Y is Boc-Ala-D-Ala.

* * * * *